United States Patent [19]

Gouge et al.

[11] Patent Number: 5,279,421
[45] Date of Patent: Jan. 18, 1994

[54] PACKAGING FOR HAZARDOUS COMPOSITIONS

[75] Inventors: Samuel T. Gouge; Leonard E. Hodakowski; Glenn C. Knudsen, all of Raleigh, N.C.; Steven F. McEvoy, Jacksonville, Fla.

[73] Assignee: Rhone-Poulenc Inc., Research Triangle Park, N.C.

[21] Appl. No.: 45,404

[22] Filed: Apr. 9, 1993

Related U.S. Application Data

[63] Continuation-in-part of Ser. No. 20,506, Feb. 22, 1993, which is a continuation-in-part of Ser. No. 874,608, Apr. 27, 1992, abandoned.

[51] Int. Cl.⁵ .............................................. B65D 83/00
[52] U.S. Cl. ................................. 206/484; 206/524.7
[58] Field of Search ................ 206/0.5, 204, 205, 219, 206/524.1, 524.2, 524.6, 524.7, 525, 568, 484, 484.1, 484.2; 71/DIG. 1; 252/315.1; 424/409, 412; 514/801, 812

[56] References Cited

U.S. PATENT DOCUMENTS

| | | | |
|---|---|---|---|
| 3,695,989 | 10/1972 | Albert | 206/524.7 |
| 3,892,905 | 7/1975 | Albert | 206/524.7 |
| 4,303,709 | 12/1981 | Olson | 383/116 |
| 4,681,228 | 7/1987 | Kerry et al. | 206/524.7 |
| 4,846,992 | 7/1989 | Fonsny | 206/524.7 |
| 4,874,656 | 10/1989 | Rantanen | 206/524.2 |

FOREIGN PATENT DOCUMENTS

| | | | |
|---|---|---|---|
| 0132726 | 2/1985 | European Pat. Off. | 206/524.7 |
| 8912587 | 12/1989 | PCT Int'l Appl. | 206/524.7 |
| 0922317 | 3/1963 | United Kingdom | 206/524.7 |

*Primary Examiner*—Jimmy G. Foster
*Attorney, Agent, or Firm*—James G. Passé

[57] ABSTRACT

The present invention relates to a containerization system comprising at least one inner water soluble bag located within an outer water insoluble bag. The inner water soluble bag contains a hazardous chemical such as an agrichemical that does not substantially dissolve the bag. The outer water soluble bag is flexible and collapsible and has a low stretchability; it is made of laminated polypropylene (outer layer) polyethylene (inner layer).

16 Claims, No Drawings

PACKAGING FOR HAZARDOUS COMPOSITIONS

This application is a continuation-in-part of U.S. Ser. No. 08/020,506 filed on Feb. 22, 1993, which is a continuation-in-part of U.S. Ser. No. 07/874,608 filed on Apr. 27, 1992, now abandoned.

BACKGROUND OF THE INVENTION

I. Field of the Invention

The invention relates to a containerization system and to containers which are particularly suitable for storing, packaging and transporting fluid agricultural chemical compounds, such as pesticides and concentrates thereof.

II. Discussion of the Prior Art

At present, most hazardous and toxic liquids are stored in metal drums or, where smaller quantities are involved, in plastic containers. Hazardous compositions, especially agricultural chemicals (agrichemical), are formulated in various compositions.

Agrichemicals in liquid form, particularly in the form of concentrates, are most convenient for farmers because of the relative ease with which they can be handled. There are, nevertheless, difficulties in handling such liquid compositions. There is a danger of spillage or leakage if holes develop in containers that are accidentally dropped and thereby crack or fail. Containers have been developed which possess great resistance to impact and shock. While such containers are secure under normal storage and handling conditions, in the event of an accident, for example during transporting, there remains an appreciable risk of spillage or leakage with rapid loss of liquid. Leakage of toxic and hazardous chemicals can create damage to the environment.

The chemical and packaging industries have long sought a secure container which provides a sufficient safeguard for those handling it, such as farmers and transporters, as well as adequate precautions for the environment.

It is known, for example, to package agrichemicals in soluble bags or sachet made from water soluble films. While considerable effort has been made and tremendous success in improving the strength of such bags, there still remains problems with the fragility of such bags resulting from sudden impact, for example from dropping.

One solution for this problem is exemplified in patent application WO 89/12590 where a water soluble bag containing a liquid agrichemical composition is encased in an outer container made of rigid or semi-rigid polymer such as polypropylene. Currently, there is a product available commercially in France called Geludose (Ciba-Geigy) which is also a water soluble bag which is stored in a rigid polymeric container. U.S. Pat. No. 3,892,905 describes water soluble packages. In that patent, overwraps are described such as single layer polyolefins cellophane glassine, foils, PVC, waxed paper and the like or combinations of those as laminates. However, the intended use of these and the selection criteria for these were based on the ability of these compositions to protect the inner bag from water or humidity contact. The only examples actually offered by the patent is a cellophane overwrap. Such external container may also break under violent shock and the broken container may have edges which may cut the water soluble bag which is inside of it.

In its working example, the prior art describes a container wherein the outer container comprises a rigid body-part (which contains the inner bag, i.e. the area within which the bag can move and a shock absorbing rigid part separated from the body part by mean of shoulder, or shock absorbing stripes wherein the inner bag cannot move and/or deform completely. In other words, a body part which is actually the outer container and another added shock absorbing part which is not part of the outside container.

When designing containers for protecting objects having a degree of fragility, rigid materials are the first choice despite the high cost compared with many flexible polymers.

An object of the instant invention is to provide a new containerization system to contain hazardous chemicals which is safe for everybody because of its increased resistance to leakage.

Another object of the instant invention is to provide a new containerization system to contain agrichemicals which is easy for the farmer to manipulate.

Another object of the instant invention is to provide a new containerization system to contain agrichemicals which is as much condensed as possible, using the least amount of space.

Another object of the instant invention is to provide a new containerization system to contain agrichemicals which is easy to open, easy to manufacture (and thus cheap), and which has a good shock absorption, that is to say, which has a good resistance to shock such as impact and blows.

Another object of the instant invention is to provide a new containerization system to contain agrichemicals which is stable both at high and low temperatures.

Another object of the instant invention is to provide a new containerization system and/or a new method to contain agrichemicals which diminishes the risks of pollution.

A further object of the present invention is to provide a containerization system which has no lids, and is easier and cheaper to manufacture and has no problem of lids coming off.

A further object of the present invention is to provide a new containerization system for agrichemicals which reduces the waste disposal of contaminated containers and overpacks.

A further object of the present invention is to provide a new containerization system for agrichemicals which allows very efficient packing and storing due to flexible, optionally flat bags.

Other objects of the invention will better appear from the following description.

An object of the invention is to avoid this risk of spill or pollution and to increase the safety of water soluble packaging of agrichemicals.

SUMMARY OF THE INVENTION

The present invention relates to a containerization system comprising a cold water soluble inner bag containing a hazardous composition, the said inner bag being contained in an outer bag made of a material which is in the form of a flexible and sealed (preferably heat sealed) polymeric laminated film having a polypropylene outer layer and polyethylene inner layer and is insoluble both in the composition (if liquid or gel) contained in the inner bag and in the solvent which may be comprised in the agrichemical composition contained in the inner bag, the polymeric film having a low stretchability.

Furthermore, in a preferred embodiment the surface of the area delimitated by the external largest outline of the inner bag, when inside the outer bag, should be at least 5% less than the surface area delimitated by the external largest outline of the effectively containing part of the outer bag when containing the inner bag.

The agrichemical composition which is contained in the inner bag of the invention may be solid, or preferably fluid. A solid composition may be in the form of powder, dust, or granules. By fluid composition, it is meant a composition which may be in the form of a liquid or a gel, or also of a solid such as powders or dusts or granules, provided that this solid can deform or even flow easily. However, the gels are preferred in this invention.

Another advantage of the flexible bags of the invention is that they have no parts able to damage other neighboring bags.

Another advantage of the flexible bags of the invention is that they have no lids which may come off due to possibly weak seals.

By polymeric film having a low stretchability, it is meant a film whose elongation at break is less than 100%, preferably less than 30%.

Due to their complete flexibility, the water insoluble bags in this invention may collapse when void. This is especially advantageous by creating less garbage for land filling than known rigid or semi-rigid outer containers.

The objects of the invention can be achieved in full or in part by means of the invention.

DETAILED DESCRIPTION OF THE INVENTION

It has been discovered that when water soluble bags are contained in a laminated outer bag that the objects of the invention can be met, especially the resistance to breakage.

The containerization system of the present invention comprises an inner water soluble bag containing a hazardous composition wherein the inner bag is contained in a sealed outer bag and the walls of the outer bag comprising a laminate of an outer layer of polypropylene and an inner layer of polyethylene.

The expression toxic or hazardous compositions, as used herein means an industrial chemical, for example an agrichemical composition, which, if released in the quantity or concentration normally in storage and shipping containers, may cause damage to the environment or be injurious to a person contacted by it and may either be in solid or liquid form, although liquid is preferred.

By outer bag, as used herein, is meant an overwrap designed for containing the inner water soluble bag and protecting it from humidity and water as well as provide an increased degree of protection from breakage when compared with known over-wraps in the art. Particularly, the overwrap comprises a laminate of an outer layer of polypropylene film and an inner layer of polyethylene film. Each polymer may contain other ingredients, i.e. additive to affect stiffness, e.g. plasticizers or for affecting other properties as desired, especially stretchability. The total thickness of the film overwrap outer bag is from about 20 to 500 microns, preferably 30 to 100 microns. The thickness of each individual layer being approximately half the total thickness although other thicknesses as desired can be chosen. The two polymeric layers can be made into a laminate by any means known in the art, for example by co-extrusion or heat laminating after individual extrusion. The outer bag is formed by sealing, preferably heat sealing the three sides of a sack leaving an opening which to place the inner sack followed by a final sealing of the fourth edge. It will be noted that when forming a seal, the inner polyethylene layers are sealed together.

The heat seals are made at an external temperature and humidity and such that maximum handling strength is achieved. This is simply done by one skilled in the art and requires a minimum of experimentation. Since temperature and humidity will of course vary with the thickness of the laminate, as will the heat temperature and contact time, this too is well within the skill of the art. After sealing, the resulting package resists damage due to impact better than other known outer wrap materials. The size is picked based on packaging consideration, but it is preferred that the inner dimensions of the overwrap are no more than 15% greater of the outer dimensions of the inner bag preferably 10%, most preferably less than 5%.

The overwrap is preferably not filled to complete capacity because the unused capacity gives additional shock resistance, i.e., resistance to breakage when dropped, transported or stored. This unused capacity may or may not contain air or inert gas. An absence of air or inert gas in the unused capacity further improves shock resistance. However in deciding how much unused capacity, or absence of air or inert gas, to provide, the advantages of shock resistance must be balanced against the need, if any, for shock resistance and the cost of providing shock resistance. For example, if the outer bag is stored and/or transported in a rigid shock absorbing container, then it may not be as helpful to provide this unused capacity.

Also, the capacity to which the outer bag is filled, and whether the unused capacity does or does not contain air is affected by whether it is desired to have the bag sink or float.

The hazardous composition of the invention and the wall of the inner bag it contains are chosen so that the composition does not substantially dissolve the wall of the bag and does not substantially permeate through it. By this, it is meant that the dissolution and permeation are each independently less than 5% more preferably less than 1%, and most preferably less than 0.5% of the total weight of the bag.

The preferred agrichemical compositions used in this invention are concentrated compositions which are supposed to be diluted with water in a spray tank before use and spraying by the farmer.

The agrichemical compositions which may be used in this invention and which may be contained in the outer or the inner container may be in different physical forms.

They may be in the form of a solid such as powders, preferably water wettable powders, or granules, preferably water dispersible granules.

The agrichemical compositions of this invention may be also in the form of a (preferably non-aqueous) liquid, such as a solution or a dispersion or an emulsion in an organic solvent; this liquid may be more or less viscous; it may be a very fluid liquid such as a liquid having a Brookfield viscosity between 100 and 1000 centipoise, or it may be a viscous liquid, such as a liquid having a Brookfield viscosity from 1,000 up to 30,000 centipoise (Measurements of viscosities in this specification are made with a Brookfield viscometer at 30° C. with a flat plate rotating at 20 revolutions per minute).

A further advantageous physical form of the agrichemical compositions of this invention is the form of an organic gel.

Gels which are of particular interest in this invention are organic gels which have viscosities of 600 to 30,000 centipoise, preferably 1,000 to 12,000 centipoise, and still more preferably 1,000 to 5,000 centipoise.

Another feature of the instant invention is an insecticidal composition and insecticidal unit wherein the storage modules (G' measured as hereafter defined, under speed of oscillations of 1 rd/s=radian per second) is in the range of 1 to 10,000 Pascal, preferably 10 to 5,000 Pascal.

The gel material which is used in this invention is essentially a material which has a phase difference phi between the controlled shear stress and the resulting shear strain such that tg(phi) is less than or equal to 1.5, preferably less than or equal to 1.2. Tg(phi) is the tangent of the phi angle (or phase difference). The measurement of phi is made by means of a dynamic rheometer. Dynamic rheometers which are appropriate to measure phi are known and available commercially. They usually have a flat fixed plate and a rotating cone or plate, or a so-called couette measuring system. Other mechanical systems are also available. Generally the choice of one system or another is made according to the recommendations of the seller of the rheometer, and is adapted to the kind of compound, gel or liquid, which is tested. The particular choice of a specific type of rheometer is something well known by one skilled in the art of rheology. A rotating plate over another plate or a cone rotation over a plate are often more appropriate when a gel or a viscous liquid is tested. When two kinds of system for the rheometer are possible, similar values of phi are actually measure. The cone (or the plate or the couette) is caused to rotate by means of a controlled speed motor; the rotation is a sinusoidal one, i.e., the strain and the angular displacement change as a sine function with time. Tg(phi) is equal to the ratio G"/G', wherein G' is the storage modules (represents the behavior of a perfect solid); G" is the loss modules (represents the behavior of a perfect liquid). G' and G" are expressed in Pascal for a given rotational speed (radian per second).

G' and G", and thus tg(phi), may depend on the amplitude of the oscillations (percentage of strain) of the rheometer; however, there is generally a so-called viscoelastic plateau whereby the values G' and G" of a gel do not depend substantially on the said amplitude. This means that in the conditions of the test under the viscoelastic plateau, the structure of the gel is maintained and no destruction of the gel into a liquid happens. Of course, the measurement of G' and G" of a gel is made under the conditions of this viscoelastic plateau, just because it corresponds to the normal gel structure which is precisely what is tested.

G' and G", and thus tg(phi), may also depend on the speed of the oscillations (time to reach the chosen percentage of strain; expressed as radian per second) of the rheometer. However, when the gel is well structured, there is not so much variation from one speed to another. In order to have a reasonable measurement of the properties of a gel, it is generally preferred to operate in conditions whereby the gel is not too much stressed, that is to say at speed such as 1 rd/s. Of course, measurements at higher speed may also be made.

It is known that a gel is generally a colloid in which the dispersed phase has combined with the continuous phase to produce a viscous, jelly-like product; it is also a dispersed system consisting typically of a high molecular weight compound or aggregate of small particles in very close association with a liquid. The gels used in this invention have basically an organic continuous phase. In contrast, most of the existing materials/gels are water-based and have an aqueous continuous phase. Furthermore, the gels used in this invention have essentially one physical phase, at least as can be seen when visually observed. Preferred gels in this invention are also gels which can be divided by cutting and whose cut parts are able to merge together by sample juxtaposition.

When the fluid agrichemical compositions contained in the inner bag of the invention is not a gel, it may be a material which has a phase difference phi between the controlled shear stress and the resulting shear strain, such that tg(phi) is greater than or equal to 1.5. More generally, it is then a liquid which has a phase difference phi between the controlled shear stress and the resulting shear strain, such that tg(phi) is grater than or equal to 5. Such liquids have generally a viscosity less than 12,000 cps.

The non aqueous agrichemical compositions which are used in this invention are preferably less than 3%, more preferably less than 1%.

The choice of the particular physical form of the agrichemicals used in this invention depends on the particular agrichemicals which are involved.

The following features, alone or in combination, constitute preferred features of the invention:

According to one feature, the hazardous product is preferably an agrichemical, or more precisely a plant protection agent (including pesticides, such as insecticides, fungicides, herbicides, acaricides or nematicides) or plant growth regulators or plant nutrients, or an adjuvant for the activity for plants as activity promoters including penetrating agents, synergists, antidotes, sticking agents, spreaders, activators, compatibility agents: adjuvants for the water soluble bags as plasticizers.

The invention is not limited to some specific agrichemicals; a list of many agrichemicals which can be used in a poly-bag system of the invention includes: fungicides such as triadimefon, tebuconazole, prochloraz, triforine, tridemorph, propioconazole, pirimicarb, iprodione, metalaxyl, bitertanol, iprobenfos, flusilazol, fosetyl, propyzamide, chlorothalonil, dichlone, mancozeb, anthraquinone, maneb, vinclozolin, fenarimol, bendicocarb, captafol, benalazyl, thiram;

herbicides (or defoliants) such as quizalopfop and its derivatives, acetochlor, metolachlor, imazapur and imazapyr, glyphosate and gluphosinate, butachlor, acifluorfen, oxyfluorfen, butralin, fluazifop-butyl, bifenox, bromoxynil, ioxynil, diflufenican, phenmedipham, desmedipham, oxadiazon, mecoprop, MCPA, MCPB, linuron, isoproturon, flamprop and its derivatives, ethofumesate, diallate, carbetamide, alachlor, metsulfuron, chlorsulfuron, chlorpyralid, 2,4-D, tribufos, triclopyr, diclofop-methyl, sethoxydim, pendimethalin, trifluralin, ametryn, chloramben, amitrole, asulam, dicamba, bentazone, atrazine, cyanazine, thiobenearb, prometryn, 2-(2-chlorobenzyl)-4,4-dimethyl-1,2-oxazolidin-3-one, fluometuron, napropamide, paraquat, bentazole, molinate, propachlor, imazaquin, metribuzin, tebuthiuron, oryzalin;

insecticides or nematicides such as ebufos, carbosulfan, amitraz, vamidothion, ethion, triazophos, propoxur, phosalone, permethrin, cypermethrin, parathion, methylparathion, diazinon, methomyl, malathion, lindane, fenvalerate, ethoprophos, endrin, endosulfan, dimethoate, dieldrin, dicrotophos, dichlorprop, dichlorvos, azinphos and its derivatives, aldrin, cyfluthrin, deltamethrin, disulfoton, chlordimeform, chlorpyrifos, carbaryl, dicofol, thiodicarb, propargite, demeton, phosalone; and plant growth regulators, such as gibberellic acid, ethrel or ethephon, cycocel, chlomequat, ethephon, mepiquat.

According to another feature, the inner bags of the invention are filled to at least 60% of capacity with the agrichemical composition, more preferably to at least 70% of capacity, still more preferably 80 to 99% of capacity and most preferably 85 to 95% of capacity.

When the bag is filled with solids, the capacity is relative to bulk volume of the solids, not the actual particle volume of the solids.

In practice the agrichemical compositions used in the instant invention generally comprises the active ingredient(s) in association with other ingredients, for example surfactants, dispersants, thickeners, antifoaming, antifreezing, gelled agents or gelling agents.

According to another feature, the inner bags used in this invention are made of a polymeric water soluble film, more precisely a cold water soluble film. Cold water soluble means soluble in water at temperature less than 35° C., generally between 5° C. and 35° C. The thickness of this film is generally between 10 and 500 microns, preferably between 20 and 100 microns.

The chemical nature of the enveloping film constituting the inner bag can vary quite widely. Suitable materials are water soluble (or possibly water dispersible) materials which are insoluble in the organic solvents used to dissolve or disperse the agrichemical active ingredient. Specific suitable materials include polyethylene oxide, such as polyethylene glycol; starch and modified starch: alkyl and hydroxyalkylcellulose, such as hydroxymethylcellulose, hydroxyethylcellulose, hydroxypropyl cellulose; carboxymethylcellulose, polyvinylethers such as poly methyl vinylether or poly(2-methoxyethoxyethylene); poly(2,4-dimethyl-6-triazinylethylene; poly(3-morpholinyl ethylene); poly(n- 1, 2,4-triazolylethylene); poly(vinylsulfonic acid); polyanhydrides: low molecular weight melamineformaldehyde resins: low molecular weight urea formaldehyde resins: poly(2-hydroxyethyl methacrylate); polyacrylic acid and its homologs. Preferably the enveloping film comprises or is made from polyvinyl alcohol (PVA). PVA is generally partially or full alcoholyzed or hydrolyzed e.g. 40–100%, preferably 80–99% alcoholyzed or hydrolyzed, polyvinyl acetate (or other ester) film: copolymers or other derivatives of such polymers can also be used.

Preferred materials for constituting the bags in this invention are polyethylene oxide or methylcellulose, or polyvinyl alcohol. When polyvinyl alcohol is used, it is advantageously a 40–100% alcoholyzed or hydrolyzed, preferably 80–99% alcoholyzed or hydrolyzed, polyvinyl acetate film.

The polymeric material constituting the wall of the inner bag may be dissolved in similar conditions in cold water (cold means less than 35° C.).

The inner bag of the containerization system of the invention may be opened preferably through an easy tearing tab. Optionally, the bag may have a notch permitting to easier tear off the tab. An advantage of polyester water insoluble bag is to permit to tear off the tab more easily than polyolefins water insoluble bags. Thus there is less risk to damage the inner bag when it has to be opened; less risk to damage includes less risk of break and leakage. This is especially important for farmers who, rather often, have wet hands or are wearing gloves and may have unsuitable moves causing damage to the bag.

For the same reasons, the water insoluble bags are preferably bags which can be easily resealed. This is easier to make with polyester films. The resealable part of the bag may have a pressure seal, such as a pressure resealable top, or a so-called zip-lock bag seal; it may be too a zippered top; this resealable top may be unzipped (opened) and rezipped (reclosed). These resoluble bags are more environment friendly embodiment of the invention because any spill of agrichemicals in the outer bag at the time the inner bag is opened may be confined inside the outer water insoluble bag.

The preparation or manufacturing of the containerization system of the invention can be done according to the know process of preparation or manufacturing of water soluble bags. As a practical manner, the first bag (that is to say the inner bag, or inner bags if more than one) is prepared from a water soluble film, optionally by partial sealing or heat sealing. Then it is filled with an agrichemical composition and the bag is finally closed.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrichemical composition contained in the inner bag, the polymeric film having a low stretchability.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag. That is to say the inner bag is able to move freely in the outer bag in such a way that if any side of the inner bag comes into close contact with the outer bag, the opposite side of the said inner bag is at a distance from the closest side of the wall of the outer bag which is at least 5% of the distance between the contacting side and the opposite non-contacting side. This allows room for the inner bag to recoil when contact is made from an abrupt impact.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrichemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, and wherein the inner bag of the containerization system of the invention may be opened through a tearing tab.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrichemical composition contained in the inner bag, the polymeric film having a low stretchability, and wherein the inner bag of the containerization system of the invention may be opened through a tearing tab.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrichemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab.

Another particular embodiment of the invention is a containerization system which comprises at least one inner cold water soluble bag containing an agrichemical composition, the containerization system further comprising and outer water insoluble bag made of a flexible and sealed (optionally heat sealed) polymeric film, and wherein the polymeric film is collapsible and has an elongation at rupture less than 100%.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, which is insoluble both in the composition in the agrichemical composition contained in the inner bag, the polymeric film having a low stretchability, and wherein the polymeric film is collapsible and has an elongation at rupture less than 100%.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and wherein the polymeric film is collapsible and has an elongation at rupture less than 100%.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrichemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and wherein the polymeric film is collapsible and has an elongation at rupture less than 100%.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, and wherein the inner bag of the containerization system of the invention may be opened through a tearing tab, and wherein the polymeric film is collapsible and has an elongation at rupture less than 100%.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrichemical composition contained in the inner bag, the polymeric film having a low stretchability, and wherein the inner bag of the containerization system of the invention may be opened through a tearing tab, and wherein the polymeric film is collapsible and has an elongation at rupture less than 100%.

Another particular embodiment of the invention is a containerization system which comprises at least one inner cold water soluble bag containing an agrichemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface are delimitated by the external largest outline of the effectively containing part of the outer bag when containing the inner bag, and wherein the inner bag of the containerization system of the invention may be opened through a tearing tab and wherein the polymeric film is collapsible and has an elongation at rupture less than 100%.

Another particular embodiment of the invention is a containerization system which comprises at least one inner cold water soluble bag containing an agrichemical composition, and containerization system further comprising an outer water insoluble bag made of a flexible and sealed (optionally heat sealed) polymeric film, which is insoluble both in the composition (if liquid or gel) contained in the inner bag and in the solvent which may be comprised in the agrichemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab, and wherein the polymeric film is collapsible and has an elongation at rupture less than 100%.

Another particular embodiment of the invention is a containerization system according to anyone of the previous embodiments wherein the agrichemical composition is solid.

Another particular embodiment of the innovation is a containerization system according to anyone of the previous embodiments wherein the agrichemical composition is fluid.

Another particular embodiment of the invention is a containerization system according to anyone of the previous embodiments wherein the agrichemical composition is a liquid or gel.

Another particular embodiment of the invention is a containerization system according to anyone of the previous embodiments wherein the agrichemical composition is a powder or a dust or granules.

Another particular embodiment of the invention is a containerization system according to anyone of the previous embodiments wherein the polymeric film has an elongation at rupture less than 30%.

Another particular embodiment of the invention is a containerization system according to anyone of the previous embodiments wherein the agrichemical is selected in the group comprising plant protection agents, pesticides, insecticides, fungicides, acaricides, nematicides, plant growth regulators, plant nutrients, or an adjutant for the activity for plants as activity promoters including penetrating agents, synergists, antidotes, sticking agents, spreaders, activators, compatibility agents, adjuvants for the water soluble bags as plasticizers.

Another particular embodiment of the invention is a containerization system according to anyone of the previous embodiments wherein the water soluble polymeric film constituting the inner bag comprises polyethylene oxide or methylcellulose, or polyvinyl alcohol.

The following examples are given for illustrative purposes and should not be understood as restricting the invention.

In these examples, the Brookfield viscosity was measured, as previously indicated, with a Brookfield viscometer which had a flat plate rotating at 20 revolutions per minute.

In all the following examples, the prepared gels had a tg(phi) of between 0.75 and 1.5.

Further information regarding general aspects of water soluble packaging may be found in the following copending applications, the disclosures of David B. Edwards, William J. McCarthy, Leonard E. Hodakowski, Chi-Yu R. Chen, Samuel T. Gouge and Paul J. Weber for "Laminated Bags for Containerization of Toxic or Hazardous Materials" filed Jun. 11, 1991; U.S. Ser. No. 07/713,682, application of Samuel T. Gouge, Leonard E. Hodakowski, Paul J. Weber and Chi-Yu R. Chen for "Gel Formulations for Hazardous Products" filed Jun. 11, 1991, U.S. Ser. No. 07/713,701, application of Leonard E. Hodakowski, Chi-Yu R. Chen, Samuel T. Gouge and Paul J. Weber for "Water Dispersible Gel Formulations" filed Jun. 11, 1991; U.S. Ser. No. 07/713,685; application of Leonard E. Hodakowski, Ricky W. Couch, Samuel T. Gouge and Robert C. Ligon for "Gel Formulations" filed Jun. 11, 1991; and U.S. Ser. No. 07/713,683, application of Leonard E. Hodakowski, Chi-Yu R. Chen, Samuel T. Gouge and Paul J. Weber for "Gel Formulations for Use in To2dc or Hazardous Product Containerization Systems" filed Jun. 11, 1991.

EXAMPLE 1

A gel was made by stirring and shaking at 50° C. a mixture of the following ingredients until they were each dissolved or dispersed:

| | |
|---|---|
| active ingredient: the herbicide 2,4-D; phenoxy benzoic acid (isooctyl ester): | 64.8% |
| solvent: aromatic solvent with flash pint of 65° C.: | 24.2% |
| adjuvants: | |
| non ionic/sulfonate blended emulsifier: | 4% |
| calcium alkylbenzene sulfonate: | 1% |
| mixture of dioctylsulfosuccinate salt and sodium benzoate | 6% |

During stirring, a dissolution or dispersion appeared, and thereafter gelation. Gelation increased as the mixture cooled to about 20° C.

The Brookfield viscosity of the gel was 3,000 centipoise.

800 g of this gel were put in a one-liter bag made of a film of PVA (88% hydrolyzed polyvinyl acetate; cold water soluble; thickness: 55 microns). The bag was partially full and had a residual inflatability of 20%. The outline of this bag was 25.4 cm long and 15 cm wide.

This bag was put in an outer bag, or overpack, whose outline was 28 cm long and 16 cm wide. The outer bag was made of a flexible laminated film made of one layer of polypropylene (outer layer) and one (inner) layer of polyethylene. Both bags were heat sealed.

The bag in the outer bag was dropped repeatedly from 0.79 m above the ground. An average of 36 drops were necessary to obtain failure of the outer bag. Even in this case, the inner bag had no failure.

The bag alone or the bag in a known rigid container had failure with a substantially less number of repeated drops, and the inner bag may be injured. When compared with other outer wraps, the invention overwrap is less likely to rupture.

What is claimed is:

1. A containerization system which comprises an inner water soluble bag containing a hazardous composition wherein the inner bag is contained in a sealed outer bag, the walls of the outer bag comprising a laminate of an outer layer of polypropylene and an inner layer of polyethylene.

2. A containerization system, according to claim 1, wherein the hazardous composition is an agricultural composition.

3. A containerization system, according to claim 1, wherein the overwrap has a low stretchability.

4. A containerization system, according to claim 1, wherein the inner dimension is no more than 15% greater than the outer dimension of the inner bag.

5. A containerization system, according to claim 4, wherein the inner dimension is no more than 10% greater than the outer dimension of the inner bag.

6. A containerization system, according to claim 5, wherein the inner dimension is no more than 5% greater than the outer dimension of the inner bag.

7. A containerization system, according to claim 1, which has a low stretchability and the inner dimension are no more than 15% of the outer dimension of the inner bag.

8. A containerization system, according to claim 1, which comprises a tearing tab.

9. A containerization system, according to claim 1, which has an elongation at rupture of less than 100%.

10. A containerization system, according to claim 1, wherein the thickness is from 20 to 500 microns.

11. A containerization system, according to claim 10, wherein the thickness is 30 to 100 microns.

12. A containerization system, according to claim 1 wherein the composition is a solid.

13. A containerization system, according to claim 1, wherein the composition is a fluid.

14. A containerization system, according to claim 1, wherein the composition is a gel.

15. A containerization system according to anyone of claims 1 to 14 wherein the agrichemical is selected in the group comprising plant protection agents, pesticides, insecticides, fungicides, herbicides, acaricides, nematicides, plant growth regulators, plant nutrients, or an adjuvant for the activity for plants as activity promoters including penetrating agents, synergists, antidotes, sticking agents, spreaders, activators, compatibility agents; adjuvants for the water soluble bags as plasticizers.

16. A containerization system according to anyone of claims 1 to 14 wherein the water soluble polymeric film constituting the inner bag comprises polyethylene oxide or methylcellulose, or polyvinylalcohol.

* * * * *